United States Patent
Subbiah et al.

(10) Patent No.: US 9,803,149 B2
(45) Date of Patent: Oct. 31, 2017

(54) COMPOUNDS AND METHODS FOR INHIBITING CORROSION IN HYDROCARBON PROCESSING UNITS

(71) Applicant: General Electric Company, Schenectady, NY (US)

(72) Inventors: Alagarsamy Subbiah, Bangalore (IN); Rebika Mayanglambam Devi, Bangalore (IN); Nimeshkumar Kantilal Patel, The Woodlands, TX (US); Muthukumar Nagu, Bangalore (IN); Rhomit Ghosh, Kolkata (IN); Sathees Kesavan, Bangalore (IN); Ashok Shankar Shetty, Trevose, PA (US); Manish Joshi, Bangalore (IN)

(73) Assignee: GEneral Electric Company, Schenectady, NY (US)

( * ) Notice: Subject to any disclaimer, the term of this patent is extended or adjusted under 35 U.S.C. 154(b) by 902 days.

(21) Appl. No.: 14/068,068

(22) Filed: Oct. 31, 2013

(65) Prior Publication Data

US 2015/0114884 A1 Apr. 30, 2015
US 2017/0204339 A9 Jul. 20, 2017

Related U.S. Application Data

(63) Continuation-in-part of application No. 13/468,638, filed on May 10, 2012.

(51) Int. Cl.
*C10G 75/04* (2006.01)
*C10G 29/20* (2006.01)
(Continued)

(52) U.S. Cl.
CPC .............. *C10G 75/04* (2013.01); *C10G 7/10* (2013.01); *C10G 19/00* (2013.01); *C10G 19/02* (2013.01);
(Continued)

(58) Field of Classification Search
CPC ....................... C10G 7/10; C10G 75/00–75/04
See application file for complete search history.

(56) References Cited

U.S. PATENT DOCUMENTS 3,472,666 A 10/1969 Foroulis
3,649,167 A 3/1972 Sawyer
(Continued)

FOREIGN PATENT DOCUMENTS

CA 2060580 A1 8/1992
CA 2122882 A1 11/1994
(Continued)

OTHER PUBLICATIONS

Angus Sales Sheet, DMAMP-80 Neutralizing Amine, Angus Chemical Company, Form 319-00021, Mar. 1, 2010, 2 pages.
(Continued)

*Primary Examiner* — Renee Robinson
(74) *Attorney, Agent, or Firm* — Wegman, Hessler & Vanderburg

(57) ABSTRACT

Treatment compositions for neutralizing acidic species and reducing hydrochloride and amine salts in a fluid hydrocarbon stream are disclosed. The treatment compositions may comprise at least one amine with a salt precipitation potential index of equal to or less than about 1.0. Methods for neutralizing acidic species and reducing deposits of hydrochloride and amine salts in a hydrocarbon refining process are also disclosed. The methods may comprise providing a fluid hydrocarbon stream and adding a treatment composition to the fluid hydrocarbon stream. The treatment compositions used may have a salt precipitation potential index of equal to or less than about 1.0 and comprise either water-soluble or oil-soluble amines.

7 Claims, 2 Drawing Sheets

(51) Int. Cl.
*C10G 7/10* (2006.01)
*C10G 19/073* (2006.01)
*C10G 75/00* (2006.01)
*C10G 75/02* (2006.01)
*C10G 19/00* (2006.01)
*C10G 19/02* (2006.01)
*C10G 21/20* (2006.01)

(52) U.S. Cl.
CPC ........... *C10G 19/073* (2013.01); *C10G 21/20* (2013.01); *C10G 29/20* (2013.01); *C10G 75/00* (2013.01); *C10G 75/02* (2013.01); *C10G 2300/4075* (2013.01); *C10G 2300/44* (2013.01); *C10G 2300/80* (2013.01)

(56) References Cited

U.S. PATENT DOCUMENTS

| | | | |
|---|---|---|---|
| 3,779,905 A | 12/1973 | Stedman | |
| 3,819,328 A | 6/1974 | Go | |
| 3,981,780 A | 9/1976 | Scherrer et al. | |
| 4,062,764 A | 12/1977 | White et al. | |
| 4,192,844 A | 3/1980 | Trace et al. | |
| 4,350,606 A | 9/1982 | Cuisia et al. | |
| 4,430,196 A | 2/1984 | Niu | |
| 4,440,625 A * | 4/1984 | Go | C10G 9/16 208/48 AA |
| 4,490,275 A | 12/1984 | Niu | |
| 4,626,411 A | 12/1986 | Nemes et al. | |
| 4,806,229 A | 2/1989 | Ferguson et al. | |
| 4,992,210 A | 2/1991 | Naeger et al. | |
| 5,114,566 A * | 5/1992 | Naeger | C10G 19/02 208/289 |
| 5,211,840 A | 5/1993 | Lehrer et al. | |
| 5,283,006 A | 2/1994 | Lehrer et al. | |
| 5,328,325 A | 7/1994 | Strohl et al. | |
| 5,387,733 A | 2/1995 | Weaver | |
| 5,590,716 A | 1/1997 | Mansfield | |
| 5,641,396 A | 6/1997 | Braden et al. | |
| 5,714,664 A | 2/1998 | Fearnside et al. | |
| 5,759,485 A | 6/1998 | Fischer et al. | |
| 5,902,515 A | 5/1999 | Kanwar et al. | |
| 5,965,785 A | 10/1999 | Braden et al. | |
| 7,381,319 B2 | 6/2008 | Lack et al. | |
| 2008/0139414 A1 | 6/2008 | Cassidy et al. | |
| 2010/0234592 A1 | 9/2010 | Leinweber et al. | |
| 2012/0149615 A1 | 6/2012 | Lack | |

FOREIGN PATENT DOCUMENTS

| | | |
|---|---|---|
| EP | 0498178 A2 | 8/1992 |
| GB | 1539645 A | 1/1979 |
| JP | 526704 A | 1/1977 |
| JP | 558460 A | 1/1980 |
| JP | 6134095 A | 2/1986 |
| JP | 6315886 A | 1/1988 |
| JP | 03150380 A | 6/1991 |
| JP | 2004211050 A | 7/2004 |
| JP | 2008184680 A | 8/2008 |
| WO | WO 2004106468 A1 | 12/2004 |
| WO | WO 2008041569 A1 | 4/2008 |
| WO | WO 2008078532 A1 | 7/2008 |
| WO | WO 2009044020 A2 | 4/2009 |
| WO | 2013130123 A1 | 9/2013 |

OTHER PUBLICATIONS

International Search Report and Written Opinion issued in connection with corresponding PCT Application No. PCT/US2014/060354 dated Jan. 14, 2015.

* cited by examiner

COMPOUNDS AND METHODS FOR INHIBITING CORROSION IN HYDROCARBON PROCESSING UNITS

FIELD OF THE INVENTION

The present invention relates to the refinery processing of crude oil. Specifically, it is directed towards the problem of corrosion of refinery equipment caused by corrosive elements found in the crude oil.

CROSS REFERENCE TO RELATED APPLICATION

The present application is a continuation in part of U.S. patent application Ser. No. 13/468,638, filed May 10, 2012 titled COMPOUNDS AND METHODS FOR INHIBITING CORROSION IN HYDROCARBON PROCESSING UNITS, and herein incorporated by reference.

BACKGROUND OF THE INVENTION

Hydrocarbon feedstocks such as petroleum crudes, gas oil, etc., are subjected to various processes in order to isolate and separate different fractions of the feed stock. In refinery processes, the feedstock is distilled so as to provide light hydrocarbons, gasoline, naphtha, kerosene, gas oil, etc.

The lower, boiling fractions are recovered as an overhead fraction from the distillation tower. The intermediate components are recovered as side cuts from the distillation tower. The fractions are cooled, condensed, and sent to collecting equipment. No matter what type of petroleum feed stock is used as the charge, the distillation equipment is subjected to the corrosive activity of acids such as $H_2S$, HCl, organic acids, and $H_2CO_3$.

Corrosion in the crude overhead distillation equipment is mainly due to condensation of hydrogen chlorides formed by hydrolysis of the magnesium chloride and calcium chloride in crude oil. Typical hydrolysis reactions may proceed as in Equations I or II:

$$MgCl_2 + 2H_2O \leftrightarrow 2HCl + Mg(OH)_2 \quad (I)$$

$$CaCl_2 + 2H_2O \leftrightarrow 2HCl + Ca(OH)_2 \quad (II)$$

Corrosive attack on the metals normally used in the low temperature sections of a refinery (i.e., where water is present below its dew point) is an electrochemical reaction generally in the form of acid attack on active metals in accordance with Equations III, IV or V:

$$\text{At the anode: } Fe \leftrightarrow Fe^{++} + 2e^- \quad (III)$$

$$\text{At the cathode: } 2H^+ + 2e^- \leftrightarrow 2H \quad (IV)$$

$$\text{At the cathode: } 2H \leftrightarrow H_2 \quad (V)$$

The aqueous phase may be water entrained in the hydrocarbons being processed and/or water added to the process for such purposes as steam stripping. These waters, regardless of source, are collectively referred to as brines. Acidity of the condensed water is due to dissolved acids in the condensate, principally HCl, organic acids, $H_2S$, and $H_2CO_3$. HCl, the most troublesome corrosive material, is formed by hydrolysis of calcium and magnesium chlorides originally present in the brines.

One of the chief points of difficulty with respect to corrosion occurs above and in the temperature range of the initial condensation of water. The term "initial condensate" as it is used herein signifies a phase formed when the temperature of the surrounding environments reaches the dew point of water. At this point a mixture of liquid water, hydrocarbon, and vapor may be present. Such initial condensate may occur within the distillation tower itself or in subsequent condensers. The top temperature of the distillation tower is normally maintained above the dew point of water. The initial aqueous condensate formed contains a high percentage of HCl. Due to the high concentration of acids dissolved in the water, the pH of the first condensate is quite low. For this reason, the water is highly corrosive.

In the past, highly basic ammonia has been added at various points in hydrocarbon refining processes in an attempt to control the corrosiveness of condensed acidic materials Ammonia, however, has not proven effective with respect to eliminating corrosion occurring at the initial condensate. It is believed that ammonia has been ineffective for this purpose because it does not condense completely enough to neutralize the acidic components of the first condensate.

Several amines, including morpholine and methoxypropylamine, have been used to successfully control or inhibit corrosion that ordinarily occurs at the point of initial condensation within or after the distillation tower. These amines or their blends are added in pure form or as an aqueous solution. The high alkalinity of these amines serves to raise the pH of the initial condensate rendering it less corrosive. The amines are added in amounts sufficient to raise the pH of the liquid at the point of initial condensation to above 4.0, and in some cases, to between 5.0 and 6.0.

These amines, however, form hydrochloride salts that deposit on the inner surfaces of hydrocarbon refining equipment. These deposits can cause both fouling and corrosion problems and are most problematic in units that do not use a water wash.

Some amines and their blends currently used produce less salt deposits on hydrocarbon refining equipment than the amines listed above. These amines are also aqueous amines and are introduced in the distillation tower or downstream of the distillation tower. These amines include picoline (U.S. Pat. No. 5,211,840) and blends comprising dimethylethanolamine and dimethylisopropanolamine, (U.S. Pat. No. 4,490,275) ethylenediamine, monoethanolamine and hexylmethylenediamine (U.S. Pat. No. 7,381,319). Additional amines include trimethylamine and N-methylmorpholine and their blends.

BRIEF DESCRIPTION OF THE INVENTION

It was surprisingly discovered that some amines are more effective at neutralizing the acidic species in hydrocarbon streams than ammonia. It was also surprisingly discovered that other amines are more effective than the comparative amines, trimethylamine and N-methylmorpholine. These effective amines also are effective at reducing deposits of amine salt species on the internal surfaces of hydrocarbon processing equipment.

Accordingly, a treatment composition is disclosed for neutralizing acidic species and reducing hydrochloride and amine salts in a fluid hydrocarbon stream. The treatment composition may comprise at least one amine with a salt precipitation potential index ("Salt PPI") of equal to or less than about 1.0. The fluid hydrocarbon stream may comprise an aqueous portion, or brine. Both the hydrocarbon stream and any aqueous portion present in the fluid hydrocarbon stream may be in a liquid phase, a vapor phase, or a combination thereof.

Suitable amines include, but are not limited to, 1,2 dimethylpropylamine, 1,4-dimethylpiperazine, N-methyldibutylamine, N-methyldipropylamine, ethylhexylamine, N-methylpyrrolidine, di-ethylhydroxylamine, dimethylcyclohexylamine, diethylpropargylamine, dimethyl-N-propylamine, di-N-propylamine, N,N,N',N'-tetramethylethylenediamine (TMED), N-methylpiperidine, 2-dimethylamino 2-methyl 1-propanol (DMAMP), N,N,N',N'-tetramethyldiaminomethane (TMMD), dimethyl tertiary butanolamine (DMTBA), dimethyl methoxypropylamine (DMMOPA), furfurylamine, and combinations thereof.

In another exemplary embodiment, a method for neutralizing acidic species and reducing hydrochloride and amine salts in a hydrocarbon stream is disclosed. The method may comprise contacting a fluid hydrocarbon stream with a treatment composition. The treatment composition may comprise at least one amine with a Salt PPI of equal to or less than about 1.0.

In yet another exemplary embodiment, a method for neutralizing acidic species and reducing deposits of hydrochloride and amine salts in a hydrocarbon refining process is disclosed. The method comprises contacting a fluid hydrocarbon stream present in the refining process with a first treatment composition after the fluid hydrocarbon stream leaves the desalter. The first treatment composition may comprise at least one oil-soluble amine. A second treatment composition with at least one water-soluble amine may be added to the fluid hydrocarbon stream as it leaves the distillation tower. Both the first and second treatment compositions may comprise at least one amine with a Salt PPI of equal to or less than about 1.0.

DETAILED DESCRIPTION OF EXEMPLARY EMBODIMENTS

Figure 1:
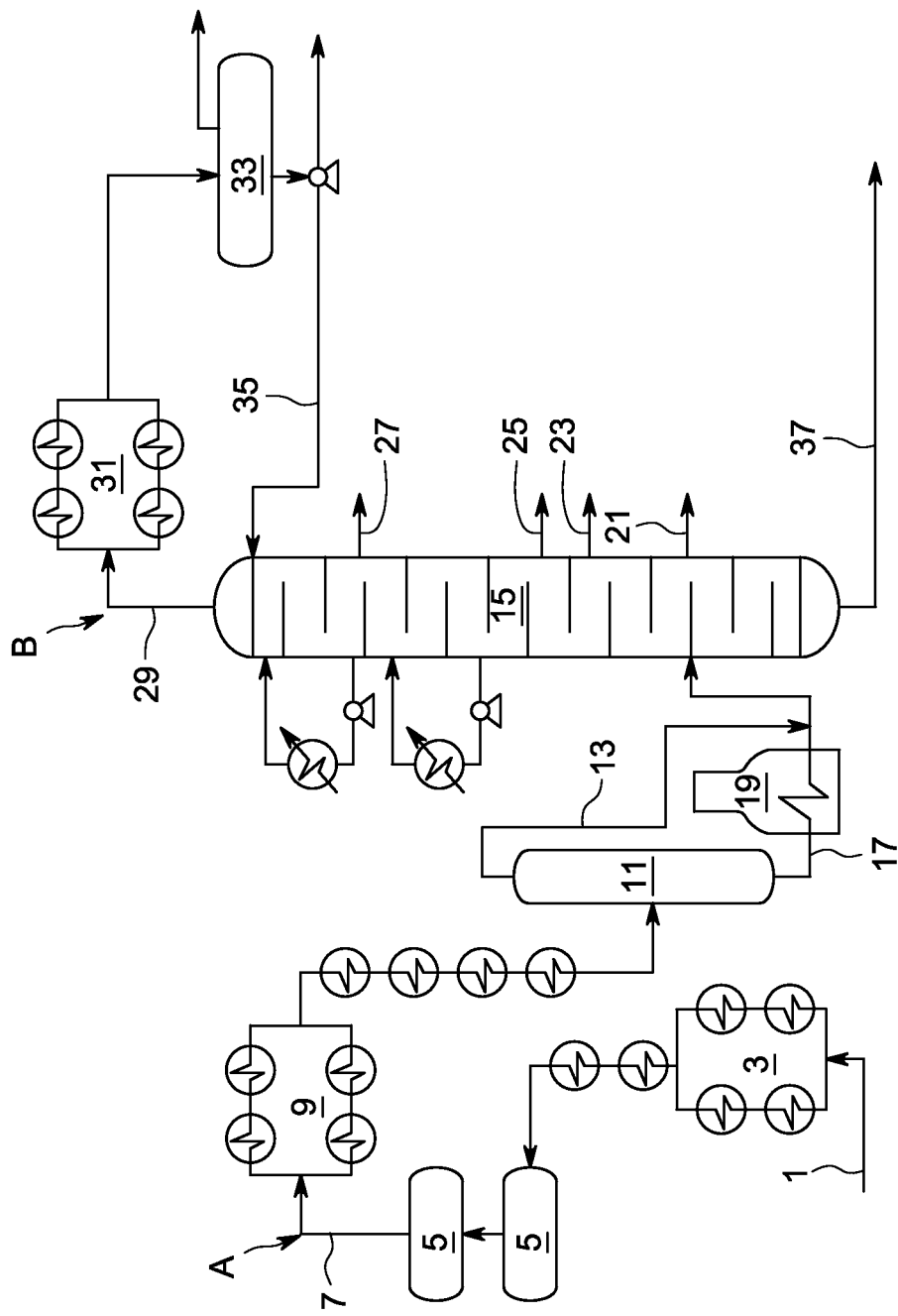
FIG. 1 shows a simplified section of a hydrocarbon refining process.

FIG. 1 (FIG. 1) shows a simplified section of a hydrocarbon refining process. Crude (1) is fed through a series of heat exchangers (3) before entering at least one desalter (5). Desalted crude (7) enters another series of heat exchangers (9) where it is preheated to about 200 to 700° F. before entering a flash drum (11), or preflash tower. The lights (13) from the flash drum may be fed directly to the distillation tower (15). The bottoms (17) from the flash drum may be fed to a direct-fired furnace (19) before they are fed to the distillation tower (15). The distillation tower is often called an atmospheric tower as it operates slightly above atmospheric pressure, typically around 1 to 3 atmospheres gauge.

The overhead distillation tower temperature usually ranges from 200 to 350° F. While in the tower, the crude is distilled into multiple fractions, also called "sidecuts". The sidecuts comprise heavy gas oil (21), light gas oil (23), diesel (25), and kerosene (27). The bottoms (37) exit the distillation tower for processing elsewhere (not shown). Naphtha vapor (29) exits the top of the distillation tower and enters a series of heat exchangers (31). The naphtha vapor then enters at least one condenser (33). A portion of the condensed naphtha stream is fed back into the top of the tower as reflux (35).

Some refining processes may not utilize a flash drum and instead feed crude directly to a direct-fired furnace. Likewise some operations have been omitted from FIG. 1 for the sake of brevity. These and other minor differences in crude refining processes do not affect the scope of the invention.

It was surprisingly discovered that some amines are more effective at neutralizing the acidic species in hydrocarbon streams than ammonia. It was also surprisingly discovered that other amines are more effective than the comparative amines, trimethylamine and N-methylmorpholine. These effective amines are also effective at reducing deposits of amine salt species on the internal surfaces of hydrocarbon processing equipment.

Without limiting this specification to any particular theory of operation, the overall efficiency of a given amine may be predicted upon assessment of several factors. One such factor is the amine-HCl salt precipitation potential index ("Salt PPI"). The Salt PPI may also be known by those in the art as the salt volatility index. These indices are merely a comparison of the precipitation potential of the amine salt to the salt of a typical neutralizing compound used in hydrocarbon refining, ammonia.

Figure 2:
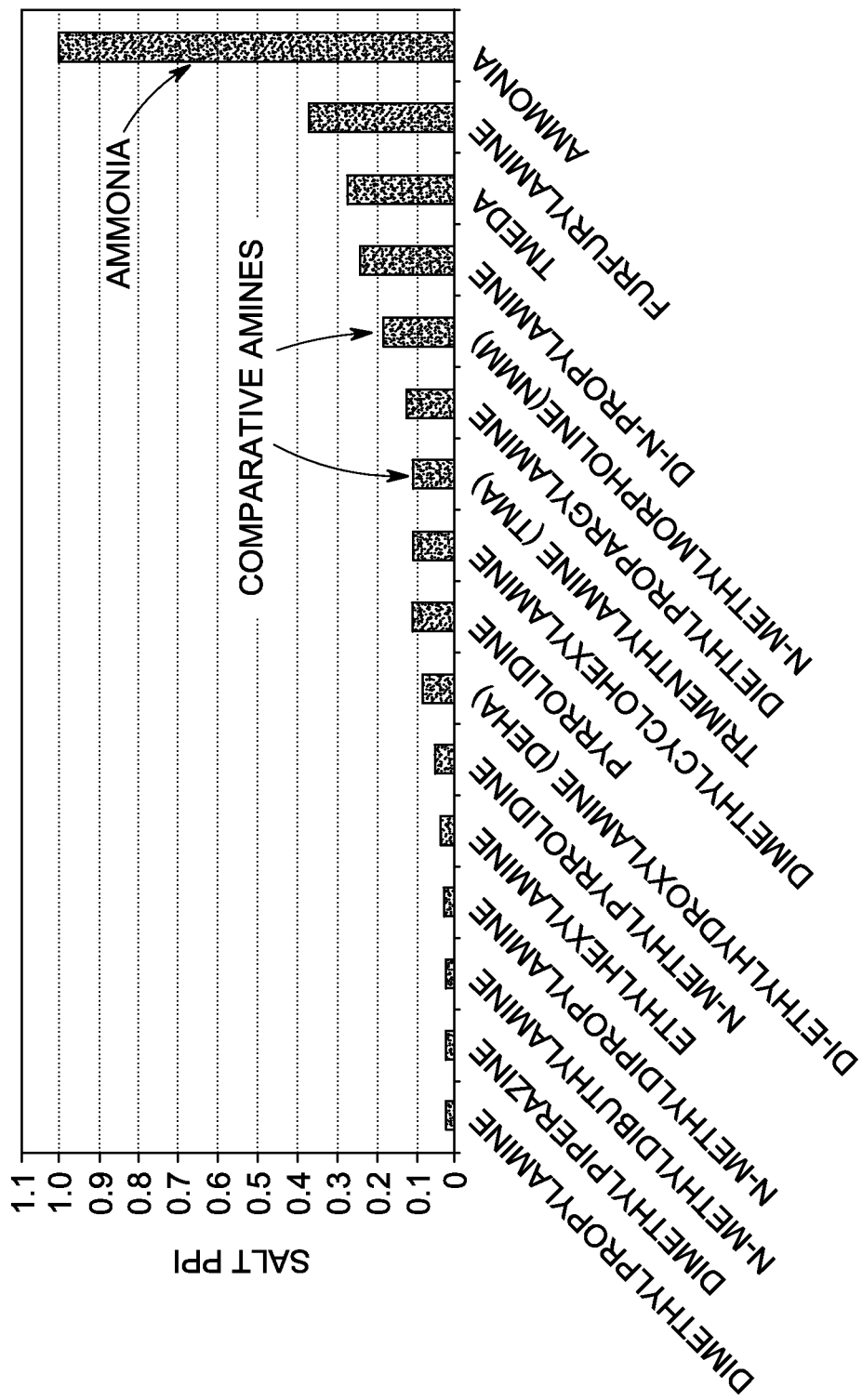
FIG. 2 shows a graph of amines and their salt precipitation potential indices.

Salt PPI may be calculated from the equation:

$$\frac{\left[\frac{p_{225°F}(NH_4Cl)}{p_{225°F}(Amine \cdot Cl)}\right] + \left[\frac{p_{300°F}(NH_4Cl)}{p_{300°F}(Amine \cdot Cl)}\right]}{2}$$

where p is the vapor pressure at either 225 or 300° F. The average Salt PPI over the 225 to 300° F. range is selected because these amines usually have the requisite volatility characteristics at typical crude overhead operating temperatures. Namely, such amines are thermally stable at temperatures typical to the refining process, yet volatile enough to condense with the initial condensate. As can be seen from the equation, the salt of the typical neutralizing compound, ammonia, is used as a benchmark. If one were to substitute the vapor pressure of ammonia for the vapor pressure of the amine in the equation, the Salt PPI would be 1.0. Effective amines are those that are as good, if not better than the typical additive, ammonia. Thus, effective amines would have a Salt PPI of equal to or less than 1.0. Other neutralizers commonly used in hydrocarbon refining are trimethylamine and N-methylmorpholine. The Salt PPI of these comparative amines is equal to, or greater than 0.1. Thus, the most effective amines would have a Salt PPI of equal to, or less than 0.1. FIG. 2 shows a graph of amines and their salt precipitation potential indices.

Accordingly, a treatment composition is disclosed for neutralizing acidic species and reducing hydrochloride and amine salts in a fluid hydrocarbon stream. The treatment composition comprises at least one amine with a salt precipitation potential index of equal to or less than about 1.0.

The fluid hydrocarbon stream may comprise an aqueous portion, or brine. Both the hydrocarbon stream and any aqueous portion present in the fluid hydrocarbon stream may be in a liquid phase, a vapor phase, or a combination thereof. Examples of fluid hydrocarbons include, but are not limited to, crude oil, natural gas, condensate, heavy oil, processed residual oil, bitumen, coker oils, coker gas oils, fluid catalytic cracker feeds and slurries, gas oil, naphtha, diesel fuel, fuel oil, jet fuel, gasoline, kerosene, crude styrene distillation tower feed, crude ethylbenzene column feed, pyrolsis gasoline, chlorinated hydrocarbons feed, or vacuum residual.

In one exemplary embodiment, at least one amine may have the structure:

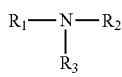

where $R_1$, $R_2$, and $R_3$ may the same or different and are H, or alkyls of 1 to 20 carbon atoms. The alkyls may be straight alkyls, branched alkyls, cycloalkyl rings, hydroxyl-substituted alkyls, or alkoxy-substituted alkyls. Said alkyls may be unsaturated. Additionally $R_1$ and $R_2$ may be interconnected by carbon or a combination of carbon and other atoms such as oxygen to form a nitrogen containing heterocyclic ring.

Suitable amines include, but are not limited to, acyclic N-alkylated alkoxy/alkanol tertiary amines which may include acyclic N-alkylated alkoxy/alkanol tertiary polyamines; cyclic amines which may include cyclic N-alkylated amines or cyclic N-alkylated tertiary polyamines or cyclic N-alkylated tertiary amines; acyclic N-alkylated tertiary amines which may include acyclic N,N'-alkylated tertiary polyamines; or combinations thereof. In another embodiment, the acyclic N-alkylated alkoxy/alkanol tertiary amine may be an acyclic N-dimethylated alkoxy/alkanol tertiary monoamine. Amines that are exemplary of this class include 2-dimethylamino 2-methyl 1-propanol (DMAMP), dimethyl tertiary butanolamine (DMTBA), and dimethyl methoxypropylamine (DMMOPA). In another embodiment, the cyclic amine may be a cyclic N-alkylated tertiary polyamine. The cyclic N-alkylated tertiary amine may be a cyclic N-methylated tertiary monoamine or diamine. Amines that are exemplary of this class may have five or six-membered rings and include 1,4-dimethylpiperazine, N-methylpyrrolidine, and N-methyl piperidine. In yet another embodiment, the acyclic N,N'-alkylated tertiary amine may be an acyclic N,N'-polymethylated tertiary diamine. Amines that are exemplary of this class include N,N,N',N'-tetramethylethylenediamine (TMED) and N,N,N',N'-tetramethyldiaminomethane (TMMD). In another embodiment the $R_1$ may be a non-carbon atom for example an oxygen as in the case of an N,N-dialkyl-hydroxylamine.

In another embodiment, the treatment composition may comprise at least one amine selected from the group consisting of 1,2 dimethylpropylamine, 1,4-dimethylpiperazine, N-methyldibutylamine, N-methyldipropylamine, ethylhexylamine, N-methylpyrrolidine, di-ethylhydroxylamine, dimethylcyclohexylamine, diethylpropargylamine, dimethyl-N-propylamine, di-N-propylamine, N,N,N',N'-tetramethylethylenediamine (TMED), N-methylpiperidine, 2-dimethylamino 2-methyl 1-propanol (DMAMP), N,N,N',N'-tetramethyldiaminomethane (TMMD), dimethyl tertiary butanolamine (DMTBA), dimethyl methoxypropylamine (DMMOPA), furfurylamine, and combinations thereof.

Another factor indicative of the overall efficiency of a given amine is the logarithm of the acid dissociation constant, pKa. Generally, amines with higher pKa values are more efficient neutralizers. Accordingly, in another embodiment, the treatment composition may comprise an amine with a pKa equal to or greater than about 5.0.

In yet another embodiment, the treatment composition may comprise an amine with a salt precipitation potential index of equal to or less than about 0.5. Alternatively, amines may have a salt precipitation potential index of equal to or less than about 0.1.

In another exemplary embodiment, a method for neutralizing acidic species and reducing deposits of hydrochloride and amine salts in a hydrocarbon stream is disclosed. The method may comprise contacting a fluid hydrocarbon stream with a treatment composition comprising at least one amine with a Salt PPI of equal to or less than about 1.0. The at least one amine may have the structure as described above.

In another method, the treatment composition may comprise at least one acyclic N-alkylated alkoxy/alkanol tertiary amine, acyclic N-alkylated alkoxy/alkanol tertiary polyamine, cyclic amine such as cyclic N-alkylated tertiary amine or cyclic N-alkylated tertiary polyamine, acyclic N,N'-alkylated tertiary polyamine, or combinations thereof. In another embodiment, the acyclic N-alkylated alkoxy/alkanol tertiary amine may be an acyclic N-dimethylated alkoxy/alkanol tertiary monoamine. The cyclic amine may include cyclic N-alkylated amines, cyclic N-alkylated tertiary polyamines, or cyclic N-alkylated tertiary amines. In one embodiment, the cyclic N-alkylated amine may be a cyclic N-methylated tertiary monoamine or diamine. In yet another embodiment, the acyclic N,N'-alkylated tertiary amine may be an acyclic N,N'-polymethylated tertiary diamine.

In another method, the treatment composition may comprise at least one amine selected from the group consisting of 1,2 dimethylpropylamine, 1,4-dimethylpiperazine, N-methyldibutylamine, N-methyldipropylamine, ethylhexylamine, N-methylpyrrolidine, di-ethylhydroxylamine, dimethylcyclohexylamine, diethylpropargylamine, dimethyl-N-propylamine, di-N-propylamine, N,N,N',N'-tetramethylethylenediamine (TMED), N-methyl piperidine, 2-dimethylamino 2-methyl 1-propanol (DMAMP), N,N,N',N'-tetramethyldiaminomethane (TMMD), dimethyl tertiary butanolamine (DMTBA), dimethyl methoxypropylamine (DMMOPA), furfurylamine, and combinations thereof.

In another method, the treatment composition may comprise an amine with a pKa equal to or greater than about 5.0. In yet another method, the treatment composition may comprise an amine with a Salt PPI of equal to or less than about 0.5. Alternatively, the amine may have a Salt PPI of equal to or less than about 0.1.

In one embodiment, a method for neutralizing acidic species and reducing deposits of hydrochloride and amine salts in a hydrocarbon stream is disclosed, wherein the treatment composition may be added to the fluid hydrocarbon stream in an amount ranging from about 1 ppm to about 1000 ppm by volume of the fluid hydrocarbon stream. In another method, the treatment composition may be added at 300 ppm to 900 ppm by volume of the fluid hydrocarbon stream. Alternatively, the treatment composition may be added at about 300 ppm to about 700 ppm.

The above ranges may vary with application, source of the hydrocarbon stream, and the corrosive species present. The fluid hydrocarbon stream, for example, may be a stream that exits the desalter in a hydrocarbon refining process. The fluid hydrocarbon stream may also be a stream that exits the distillation tower (fluid overhead stream) of a hydrocarbon refining process. In the case of the hydrocarbon stream being a stream that exits the distillation tower, the hydrocarbon stream can contain up to 10% brine, such as 0.1% to 10% brine by volume. HCl may be present at about 0.1 ppm to about 2000 ppm by volume relative to the brine and at about 0.1 ppm to about 200 ppm by volume relative to the hydrocarbon stream. The molar ratio of the treatment composition to HCl present in the fluid hydrocarbon stream may range from about 1:1 to about 5:1. Alternatively, the molar ratio may be about 1:1-1.3:1. In one embodiment, the treatment composition may be added at about 0.1 to about 1000 ppm by volume of the fluid hydrocarbon stream as it exits the distillation tower. In yet another embodiment, the treatment composition may be added at about 0.1 to about 200 ppm by volume of the fluid hydrocarbon stream as it exits the distillation tower. These ranges are effective even if other corrosive species, such as $H_2S$, are present in the hydrocarbon stream.

It was also surprisingly discovered that the effectiveness of some amines may be increased by selecting the addition point in the hydrocarbon refining process. It was also surprisingly discovered that there was a correlation between the addition point and the amine's solubility in oil or water. The effectiveness of oil-soluble amines may be increased by adding them to the fluid hydrocarbon stream as it leaves the desalter. The effectiveness of water-soluble amines may be increased by adding them to the fluid hydrocarbon stream as it leaves the distillation tower.

Accordingly, another exemplary embodiment discloses a method where the treatment composition comprises at least one water soluble amine. In another embodiment, the treatment composition is added to a fluid hydrocarbon stream after it leaves the distillation tower of a hydrocarbon refining process (FIG. 1, B).

Another exemplary embodiment discloses a method where the treatment composition comprises at least one oil soluble amine. In another embodiment, the treatment composition is added to a fluid hydrocarbon stream after it leaves the desalter of a hydrocarbon refining process (FIG. 1, A).

In yet another exemplary embodiment, a method for neutralizing acidic species and reducing deposits of hydrochloride and amine salts in a hydrocarbon refining process is disclosed. The method comprises contacting a fluid hydrocarbon stream present in the refining process with a first treatment composition after the fluid hydrocarbon stream leaves the desalter. The first treatment composition may comprise at least one oil-soluble amine. A second treatment composition with at least one water-soluble amine may be added to the fluid hydrocarbon stream as it leaves the distillation tower. Both the first and second treatment compositions may comprise at least one amine with a Salt PPI of equal to or less than about 1.0.

Another exemplary embodiment discloses a method wherein at least one water-soluble amine is a member selected from the group consisting of 1,2 dimethyl propylamine, 1,4-dimethylpiperazine, N-methylpyrrolidine, diethylhydroxylamine, dimethyl-N-propylamine, N,N,N',N'-tetramethylethylenediamine, 2-dimethylamino 2-methyl 1-propanol, N-methyl piperidine, N,N,N',N'-tetramethyldiaminomethane (TMMD), dimethyl tertiary butanolamine (DMTBA), dimethyl methoxypropylamine (DMMOPA), and furfurylamine. Yet another method discloses a method wherein at least one oil-soluble amine is a member selected from the group consisting of N-methyldibutylamine, N-methyldipropylamine, ethylhexylamine, dimethylcyclohexylamine, diethylpropargylamine, and di-N-propylamine.

Other embodiments disclose methods wherein at least one water-soluble or oil-soluble amine may have a pKa of equal to or greater than about 5.0. Yet other embodiments disclose methods wherein at least one water-soluble or oil-soluble amine may have a Salt PPI of equal to or less than about 0.5. Alternatively, the Salt PPI may be equal to or less than about 0.1.

EXAMPLES

Several amines were tested to determine their efficiencies in neutralizing acidic species and reducing deposits of hydrochloride and amine salts. The neutralization efficiency of these amines was tested using two-phase titration. For each amine tested, a titrand (100 ml) was placed in a flask. The titrand was designed to simulate an initial condensate and comprised 90 vol % naphtha and 10 vol % acidic water. The titrand was heated to 100° C. and maintained at that temperature while amine titrant was added to the flask. The resulting pH at different amine titrant concentrations are summarized in Table 1.

As shown in Table 1, all of the amines have a pKa greater than 5.0. Also shown in Table 1, all of the effective amines have a lower Salt PPI than the ammonia benchmark of 1.0. Other effective amines have a Salt PPI equal to, or lower than at least one of the comparative amines.

TABLE 1

| Amines | Solubility Oil/Water | pKa | Salt PPI | Neutral. Efficiency pH at 250 ppm | 500 ppm | 1000 ppm |
|---|---|---|---|---|---|---|
| Effective Amines | Salt PPI less than ammonia benchmark | | | | | |
| di-N-propyl amine | Oil | 10.91 | 0.24 | 2.2 | 3.0 | 7.6 |
| N,N,N',N'-tetramethylethylenediamine (TMED) | Water | 8.97 | 0.27 | 4.7 | 6.7 | 8.3 |
| Furfurylamine | Water | 8.89 | 0.38 | 2.6 | 6.5 | 8.5 |
| Comparative Amines | | | | | | |
| Trimethylamine (TMA) | Water | 9.76 | 0.10 | 2.6 | 8.0 | 8.8 |
| N-methylmorpholine (NMM) | Water | 7.10 | 0.18 | 2.4 | 5.4 | 6.8 |
| Effective Amines | Salt PPI less than at least one comparative amine | | | | | |
| 1,2 Dimethyl propyl amine | Water | 9.90 | <0.1 | 1.4 | 8.5 | 9.6 |
| 1,4-dimethylpiperazine | Water | 8.20 | <0.1 | 3.7 | 5.5 | 7.6 |
| N-methyldibutylamine | Oil | 10.31 | <0.1 | 1.9 | 2.0 | 5.0 |
| N-methyldipropylamine | Oil | 10.09 | <0.1 | 2.4 | 2.8 | 5.6 |
| Ethyhexylamine | Oil | 9.0 | <0.1 | 2.2 | 2.7 | 5.3 |
| N-methylpyrrolidine | Water | 10.32 | <0.1 | 2.2 | 6.8 | 8.1 |
| Diethylhydroxylamine | Water | 5.61 | <0.1 | 2.4 | 4.1 | 5.0 |
| Dimethylcyclohexylamine | Oil | 10.00 | 0.10 | 1.8 | 1.9 | 5.2 |
| Diethylpropargylamine | Oil | 7.70 | 0.12 | 2.2 | 3.6 | 5.9 |

A second set of tests were performed using some of the effective amines above. Additional tertiary amines were also tested and found to be effective. The additional tertiary amines were N-methyl piperidine, 2-dimethylamino 2-methyl 1-propanol ("DMAMP") in an azeotropic solution comprising 80 wt % amine, N,N,N',N'-tetramethyldiamino methane ("TMMD"), dimethyl tertiary butanolamine ("DMTBA"), and dimethyl methoxypropylamine ("DMMOPA"). The neutralization efficiency of these amines was tested using two-phase titration. For each amine tested, a titrand (100 ml) was placed in a flask. The titrand was designed to simulate an initial condensate and comprised 90 vol % naphtha and 10 vol % acidic water. The titrand was heated to 100° C. and maintained at that temperature while amine titrant was added to the flask. The tests were repeated 3 times in the second set of tests. The resulting pH at different amine titrant concentrations are summarized in Table 2. The data in Table 2 are the averages of the 3 repeated tests.

As shown in Table 2, all of the amines have a pKa greater than 5.0. Also shown in Table 2, all of the effective amines have a lower Salt PPI than the ammonia benchmark of 1.0.

with a carrier. The carrier may be an organic or aqueous solvent, depending on the amines used and their solubility in oil and water. The treatment composition may be present in a range from about 5 wt % to about 95 wt % based on a total weight of the solution. In another embodiment, the treatment composition may range from about 25 wt % to about 75 wt % based on a total weight of the solution. Alternatively, the treatment composition may range from about 40 wt % to about 60 wt %.

When water-soluble amines are used, the carrier may comprise water. When oil-soluble amines are used, the carrier may comprise at least one non-polar organic solvent. Suitable non-polar organic solvents include, but are not limited to, naphtha, heavy aromatic naphtha, pentane, cyclopentane, hexane, cyclohexane, benzene, ethyl benzene, 1,2, 4-trimethyl benzene, toluene, xylene, cumene, 1,4-dioxane, chloroform, diethyl ether, and methyl esters of fatty acids (biodiesel).

An exemplary treatment composition may have a formulation as listed in Table 3.

TABLE 2

| Amines | Solubility Oil/Water | pKa | Salt PPI | Neutral. Efficiency pH at | | | Boiling Point ° C. |
| --- | --- | --- | --- | --- | --- | --- | --- |
|  |  |  |  | 250 ppm | 500 ppm | 1000 ppm |  |
| Comparative Amines |  |  |  |  |  |  |  |
| Trimethylamine (TMA) | Water | 9.76 | 0.10 | 2.6 | 8.0 | 8.8 | 2.87 |
| N-methylmorpholine (NMM) | Water | 7.10 | 0.18 | 2.4 | 5.4 | 6.8 | 116 |
| Effective Amines | Salt PPI less than at least one comparative amine |  |  |  |  |  |  |
| 2-Dimethylamino 2-methyl 2- propanol (DMAMP) 80% azeotrope soln | Water | 10.2 | 0.27 | 2.3 | 6.3 | 9.5 | 98 |
| N,N,N,N-tetramethylethylene diamine (TMED) | Water | 8.97 | 0.48 | 4.7 | 6.7 | 8.3 | 122 |
| N-methyl piperidine | Water | 10.08 | 0.24 | 2.1 | 7.5 | 8.1 | 107 |
| 1,2 Dimethyl propyl amine | Water | 9.90 | 0.30 | 1.4 | 8.5 | 9.6 | 87 |
| 1,4-dimethylpiperazine | Water | 8.20 | 0.18 | 3.7 | 5.5 | 7.6 | 132 |
| N-methylpyrrolidine | Water | 10.32 | 0.10 | 2.2 | 6.8 | 8.1 | 81 |
| N,N,N',N'-tetramethyldiamino-methane (TMMD) | Water |  | 0.30 | 7.54 | 8.87 | 9.25 | 85 |
| Dimethyl tertiarybutanolamine (DMTBA) | Water | 8.9 | 0.32 |  |  |  | 150 |
| Dimethyl methoxypropylamine (DMMOPA) | Water | 9.5 | 0.20 |  |  |  | 124 |

Exemplary treatment compositions may have at least one amine as described above. Alternatively, the exemplary treatment compositions may have two or more of the amines described above. In yet another embodiment, the exemplary treatment compositions may comprise one or more of the amines described above as well as one or more amines that are known corrosion inhibitors. The treatment composition may be added to the hydrocarbon stream as 100% actives, or it may be added in to the hydrocarbon stream in solution

TABLE 3

| Amines | Solubility Oil/Water | wt % |
| --- | --- | --- |
| 1,4-dimethylpiperazine | Water | 30-70 |
| N-methylpyrrolidine | Water | 30-70 |

Another exemplary treatment composition may have a formulation as listed in Table 4.

TABLE 4

| Amines | Solubility Oil/Water | wt % |
| --- | --- | --- |
| N-methylmorpholine (NMM) | Water | 45-50 |
| 1,4-dimethylpiperazine | Water | 5-10 |
| N-methylpyrrolidine | Water | 40-50 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for neutralizing acidic species and reducing deposits of hydrochloride and amine salts in a hydrocarbon refining process comprising:
    (a) contacting a fluid hydrocarbon stream present in said refining process with a first treatment composition after said fluid hydrocarbon stream leaves a desalter of said hydrocarbon refining process, said first treatment composition comprising at least one oil-soluble amine with a salt precipitation potential index of equal to or less than about 1.0; and
    (b) adding a second treatment composition to said fluid hydrocarbon stream after said fluid hydrocarbon stream leaves a distillation tower of said hydrocarbon refining process, said second treatment composition comprising at least one water-soluble amine with a salt precipitation potential index of equal to or less than about 1.0; wherein said at least one water-soluble amine is a member selected from the group consisting of 1,2 dimethylpropylamine, 1,4-dimethylpiperazine, N-methylpyrrolidine, di-ethylhydroxylamine, dimethyl-N-propylamine, N,N,N',N'-tetramethylethylenediamine (TMED), 2-dimethylamino 2-methyl 1-propanol (DMAMP), N-methyl piperidine, N, N, N', N'-tetramethyldiaminomethane (TMMD), dimethyl tertiary butanolamine (DMTBA), dimethyl methoxypropylamine (DMMOPA), furfurylamine, and combinations thereof.

2. The method in claim 1, wherein said water-soluble amine comprises 1,4-dimethylpiperazine and/or N-methylpyrrolidine.

3. The method of claim 1, wherein said at least one oil-soluble amine is a member selected from the group consisting of N-methyldibutylamine, N-methyldipropylamine, ethylhexylamine, dimethylcyclohexylamine, di-ethylpropargylamine, di-N-propylamine, and combinations thereof.

4. The method of claim 1, wherein said at least one water-soluble amine has a pKa equal to or greater than about 5.0.

5. The method of claim 1, wherein said at least one oil-soluble amine has a pKa equal to or greater than about 5.0.

6. The method of claim 1, wherein said at least one water-soluble amine has a salt precipitation potential index of equal to or less than about 0.5.

7. The method of claim 1, wherein said at least one oil-soluble amine has a salt precipitation potential index of equal to or less than about 0.5.

* * * * *